(12) United States Patent
Hektner et al.

(10) Patent No.: US 6,991,617 B2
(45) Date of Patent: Jan. 31, 2006

(54) VASCULAR TREATMENT METHOD AND DEVICE

(76) Inventors: Thomas R. Hektner, 825 Navajo Rd., Hamel, MN (US) 55340; Edward S. Andrle, 2831 Benton Blvd., Minneapolis, MN (US) 55416; Chad Kugler, 2658 138th Ave. NW., Andover, MN (US) 55304; Matt Olson, 5805 32nd Ave. N., Crystal, MN (US) 55422

(*) Notice: Subject to any disclaimer, the term of this patent is extended or adjusted under 35 U.S.C. 154(b) by 0 days.

(21) Appl. No.: 10/645,013

(22) Filed: Aug. 21, 2003

(65) Prior Publication Data

US 2004/0064093 A1   Apr. 1, 2004

Related U.S. Application Data

(60) Provisional application No. 60/405,022, filed on Aug. 21, 2002, provisional application No. 60/427,195, filed on Nov. 18, 2002, provisional application No. 60/407,051, filed on Aug. 30, 2002.

(51) Int. Cl.
*A61M 31/00* (2006.01)

(52) U.S. Cl. .......................... 604/103.01; 604/103.08; 604/103.03

(58) Field of Classification Search ........... 604/103.01, 604/103.02, 103.03, 103.05, 103.06, 103.08, 604/508, 509
See application file for complete search history.

(56) References Cited

U.S. PATENT DOCUMENTS

| | | | |
|---|---|---|---|
| 6,210,392 B1 * | 4/2001 | Vigil et al. | 604/507 |
| 6,283,947 B1 * | 9/2001 | Mirzaee | 604/264 |
| 6,695,830 B2 * | 2/2004 | Vigil et al. | 604/509 |

* cited by examiner

*Primary Examiner*—Michael J. Hayes
(74) *Attorney, Agent, or Firm*—Beck & Tysver, P.L.L.C.

(57) ABSTRACT

An intravascular catheter with micro spines that penetrate arterial wall to delivery drug or mechanical injury to the vessel wall inducing a "stent" like healing process in the vessel.

2 Claims, 6 Drawing Sheets

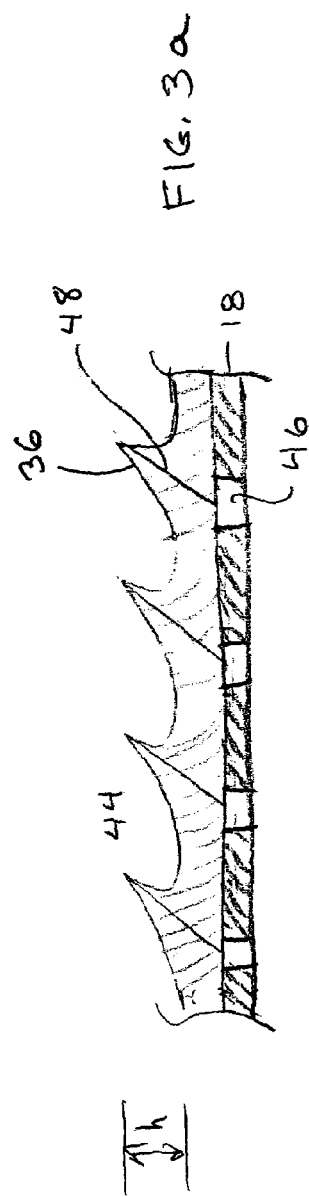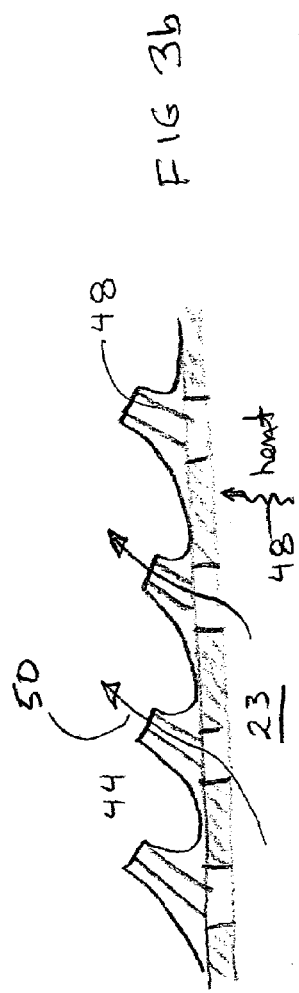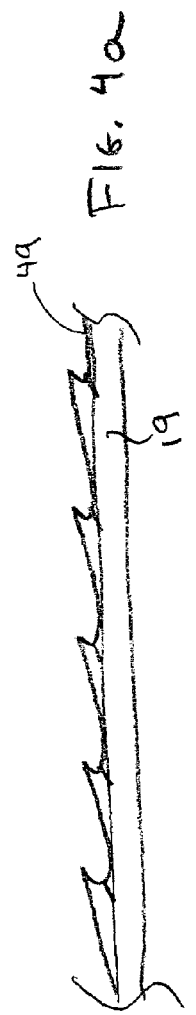

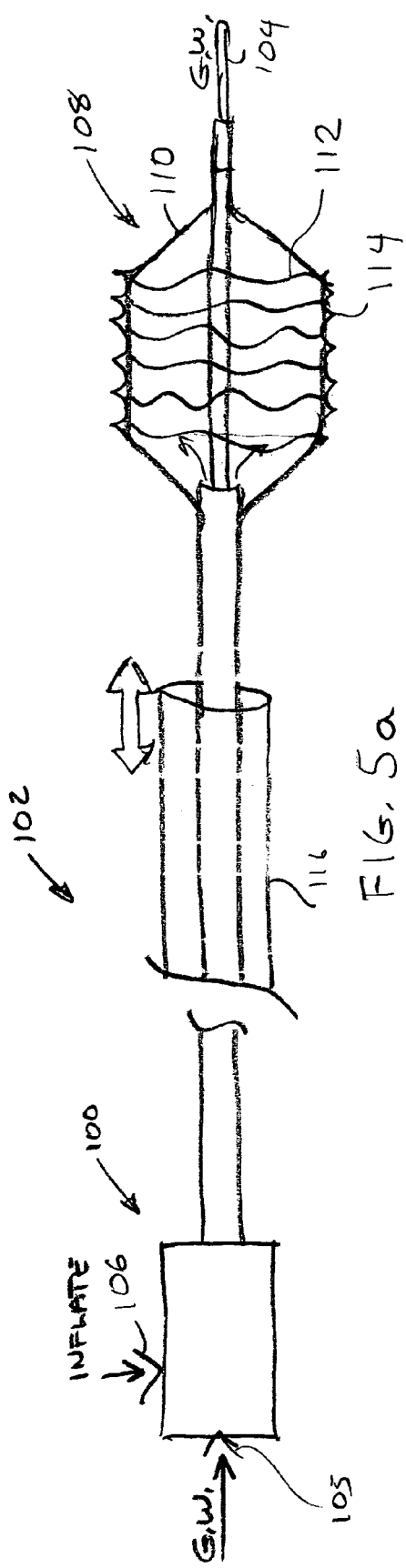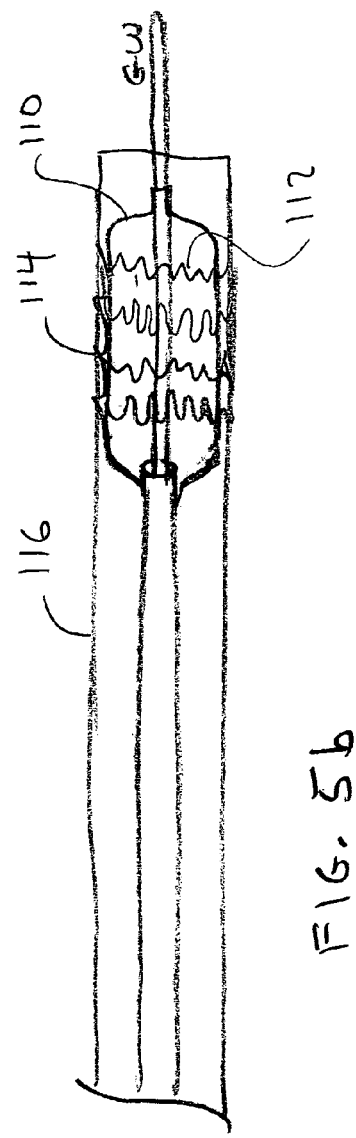
FIG. 5a
FIG. 5b

VASCULAR TREATMENT METHOD AND DEVICE

CROSS REFERENCE TO RELATED CASES

The present application incorporates by reference in their entirety and claims the benefit of the filing dates of U.S. Provisional Patent Application No. 60/405,022 filed Aug. 21, 2002, entitled Micro syringe drug delivery device and method; U.S. Provisional Patent Application No. 60/427,195 filed Nov. 18, 2002, entitled "Controlled Injury Balloon"; U.S. Provisional Patent application 60/407,051 filed Aug. 30, 2002 entitled "Drug Delivery using Shape Memory Polymers".

FIELD OF THE INVENTION

The present invention relates to devices and methods for the treatment of blood vessels and is particularly directed to the treatment of arterial vessels in the heart by the insertion of micro-spines or micro-spikes into the vessel wall from the interior or lumen of the vessel. The spines or spikes may be hollow and may be used to inject drugs into the walls of the vessel.

BACKGROUND OF THE INVENTION

The now classic treatment for stenotic lesions in the arterial system of the heart is either angioplasty followed with stent placement or simultaneous ballooning and stent expansion sometimes referred to as "direct stenting". The stent is deployed and it acts as a scaffold to support and maintain the vessel in an "open" condition. This implant is typically expanded beyond the nominal diameter of the native artery to allow for the elastic recoil and proliferative smooth muscle response of the injured vessel wall. Although the usage of stents is widespread it is widely acknowledged that the restenosis rate for stented vessels is high for many categories of lesions.

Recently drug coated and drug eluting stents have been introduced to the marketplace and these combination devices promise to lower the rate of restenosis through the action of the drug and its impact on the healing response to the injury caused by the actions of angioplasty and stenting.

In addition to stent placement and angioplasty, local drug delivery has been proposed as a therapy. Typically such drug delivery is transmural or through the tissue of a vessel to an intravascular location within the wall itself. It has been presumed that the drug will remain at that targeted location longer and more effectively than a drug delivered to the target via the moving blood stream.

As of mid-2002, anti cancer agents and antibiotics have been delivered to coronary arteries via drug eluting stents. A multitude of agents such as Rapamycin analogs, Taxol/Taxan, Actinomycin D, antisense dexamethasone, Angiopeptin Batimistat, Translast, Halofuginon, nicotine, heparin, and ASA have been or are currently under consideration as deliverable from the surface or from within voids in a stent wall or stent coating.

Research has been conducted to determine dosage, dose delivery rate, drug action control, drug take up and time duration of delivery as parameters. Also the desirability of targeting of specific cell communities within the arterial wall has been explored. Treatment site selection and drug retention have been explored with reference to the endothelium, intima, media, adventia as well as vasa vasorum of the target vessel have been investigated.

This background reflects the current practice of "treating" stenotic lesions that severely impair blood flow through the vessel. The question remains of whether or not to treat vessels that are not hemodynamically significant but appear to have a lesion or vulnerable plaque at risk of rupture. When the interventional cardiologist's diagnosis shows which of these non-occlusive lesions are candidates for treatment conventional stenting may not be an optimal choice. However delivery of drugs or other non-drug treatments from a catheter based platform may be a desirable methodology. At present there is no effective interventionally based therapy for these "vulnerable" regions and lesions other than stenting.

SUMMARY OF THE INVENTION

The present invention includes a balloon device having micro "spines" and "spikes" on its outer surface which can controllably penetrate the wall of a blood vessel for the purpose of providing a treatment to selected and targeted cells within that wall.

The invention also includes a method for creating a "drug eluting stent" like healing process without the introduction of a conventional drug coated stent into the vessel. The invention allows a physician to impart the same therapeutic "injury" as an implanted stent using conventional balloon delivery methodology eliminating the need to leave behind the metal implant. Another goal of the invention is to precisely control the depth of penetration of the micro spines so as to selectively treat a specific layer of cells within the arterial wall.

The invention allows treatment of an entire segment of arterial wall during a single balloon intervention. The catheter can be sequentially advanced down the vessel, and periodically inflated. This action will cause the micro spines to penetrate the wall with each subsequent balloon deployment. As an alternative the balloon may be lightly inflated and dragged along the vessel.

In a preferred embodiment it is preferred to deliver a controlled dose of a drug into the vessel wall. In operation, the device delivers a balloon based therapy coupled with the simultaneous delivery of a drug. The balloon is capable of delivering various amounts of pressure to the wall of the artery while the drug can be delivered to various depths of the wall. The coordination of reservoir pressure and spine depth will control the location of drug delivery. For example the drug can be delivered to the endothelial layer, the neointima, the media or advential layers of the vessel.

The injection process results in a modest injury to the vessel wall. The action of the spikes or spines will emulate the injury from a stent placement. The adjunctive drug delivery treats the vessel injury or the underlying vessel disease. Examples for proposed drugs are given in the text. In the preferred mode the simultaneous delivery of injury and drug ensures that the drug is delivered to the correct site.

As an alternative, in some applications the device and method can be used to prepare or treat a future site for a conventional stent. In this instance the preferred device and method can be used to deliver a drug to permit the use of a bare metal stent instead of a conventional drug coated stent. The device and method can also be in conjunction with or as an alternative to conventional angioplasty.

In the "stentless" method the vessel intervention can be revised at a future time with a stent if required. This intermediate treatment modality is the most preferred way to practice the invention.

The preferred device incorporates multiple spines which may be fabricated from superelastic metal or shape memory plastic. These spines are located on the exterior surface of a treatment or therapy balloon. The preferred construction includes drug reservoirs located within wall spaces in the balloon. Alternatively, drug reservoirs may be located within the spines themselves. Hydraulic forces associated with balloon inflation can be utilized to displace and force the drug through the surface of the therapy balloon. The preferred form of the device limits the spines to a controlled depth that is less than the total vessel wall thickness so that the spine injury and drug deliver site is intentionally intramural.

Another form of the catheter can include spines or spikes that are combinations of solid and hollow configurations. The hollow spines can deliver the agent and the solid spines can provide spaces and injury/targets for the drug to act upon.

A variation of the solid spine design can deliver drug which has been coated onto the spine during manufacture.

BRIEF DESCRIPTION OF THE DRAWINGS

Throughout the several figures identical reference numerals are used to indicate identical structure in the representative embodiments wherein:

FIG. 3a is a view of a portion of the shape memory polymer surface;

FIG. 3b is a view of a portion of the shape memory polymer surface;

FIG. 4a is a view of a portion of the shape memory polymer surface;

FIG. 4b is a view of a portion of the shape memory polymer surface;

FIG. 5a is a view of a portion of second embodiment of the device;

FIG. 5b is a view of a portion of second embodiment of the device;

DETAILED DESCRIPTION

Figure 1:
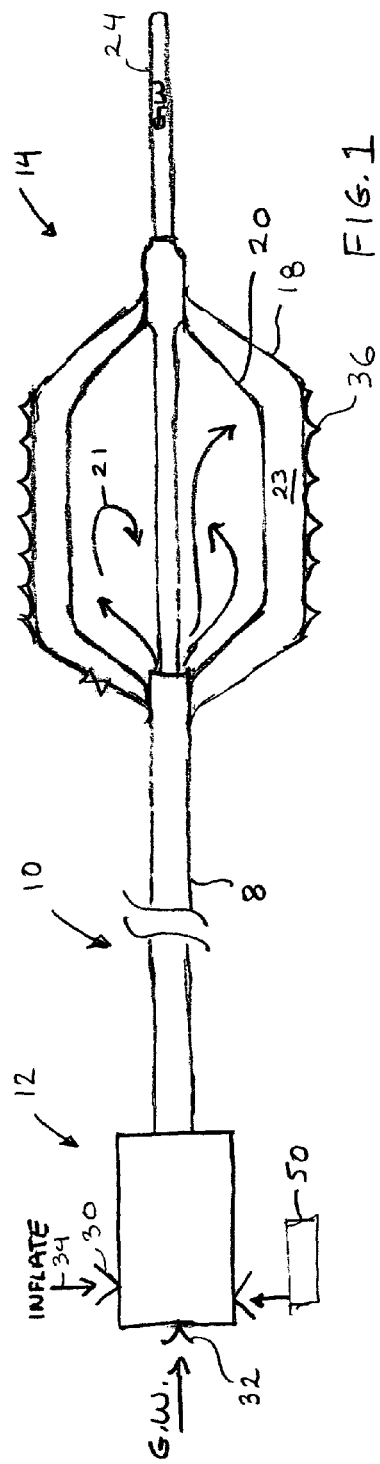
FIG. 1 is a schematic view of a first embodiment of the device.

FIG. 1 shows the device 10 in isolation. The device has an elongate catheter body 8 with a proximal end 12 and a distal end 14. The device 10 will be approximately 135 cm long as is customary in this field, and the device is shown in fragmentary view and is not to scale to emphasize certain features of the device 10.

The proximal end 12 includes a port 30 for fluid injection represented by fluid arrow 34. The fluid 34 may be heated or cooled with a heater or other energy transfer device 50. The heater embodiment supplies heat to the inflation fluid 34 that in the preferred embodiment activates the shape memory polymer surface 18 of the distal end 14 of the device. In this first embodiment the device 10 the proximal end may have a guide wire lumen port 32 for receiving a guidewire 24. It must be understood that various techniques can be used to heat or cool the fluid to activate or deactivate the polymer surface.

Shape memory polymers including preferred polyurethanes are available for Mitsubishi Industries among others. These materials and their properties are well known and are commercially available.

The distal end 14 of the device 10 shows two nested concentric balloons. The interior deployment balloon 20 communicates with the fluid inflation source through an appropriate lumen in the catheter body 8. In general the fluid 21 when injected inflates the balloon 20 that in turn moves the walls of the exterior deployment balloon 18 into contact with the vessel walls (see FIG. 2). The space between the interior and exterior deployment balloons operates as a reservoir 23 to hold a drug or other therapy agent. The drug reservoirs may alternatively be manufactured as integral spaces within the walls of either the interior or exterior balloon.

In general the maximal diameter or "size" of the interior balloon 20 and the exterior balloon 18 together form the "injector" for forcing the drug out of the reservoir 23 through a micro spine structure.

The external surface of the exterior balloon 18 is preferably a thermally activated surface with a very small feature size spine structure. In the figure the spines typified by spine 36 are shown in exaggerated scale to emphasize their position and operation.

Figure 2:
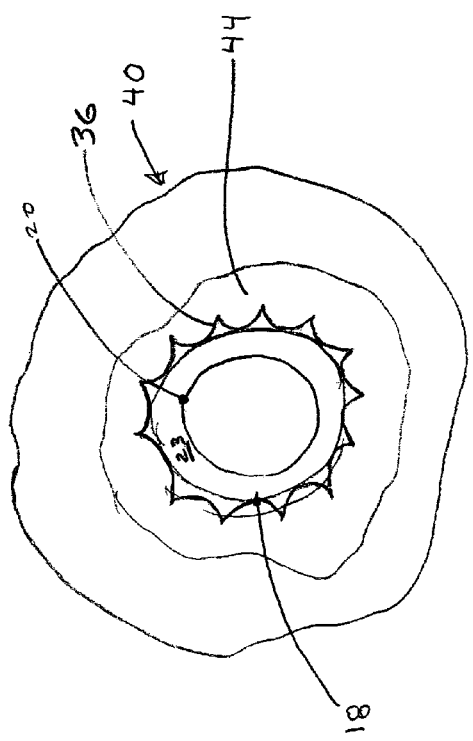
FIG. 2 is a cross section of the distal portion of the first embodiment of the device in a blood vessel.

FIG. 2 shows the distal portion of the device in cross section in a vessel 40. The spines typified by spine 36 are shown engaged with the neotintima layer 44 of the vessel 40 having passed through the thin endothelial layer of the vessel 40.

FIG. 3a shows one preferred construction for the micro spine structure. In this embodiment the balloon material is perforated as indicated by aperture 46. Although the aperture is aligned with the spine 36 in the figure for clarity of description it is to be appreciated that the apertures or pores in the balloon material 18 will statistically align with the many spines on the surface. Each spine is formed from a shape memory plastic or polymer forming spikes or spines. The average height of the spines is expected to range from 10 to 250 microns Each spine has a lumen 48 that is closed off as seen in FIG. 3a at a specific temperature range.

FIG. 3b shows the thermal surface of FIG. 3a activated by heat 48 conducted from the inflation fluid through the reservoir 23. Each spine lumen will open allowing drug 50 to exit the reservoir and enter the tissue shown in the figure s the neointima 44.

As reported in the medical and scientific literature drugs suitable for this application have included anti cancer agents and antibiotics. In general it is expected that all of the drugs that have been delivered to coronary arteries via drug eluting stents are candidate drugs for this device. A multitude of agents such as Rapamycin analogs, Taxol/Taxan, Actinomycin D, antisense dexamethasone, Angiopeptin Batimistat, Translast, Halofuginon, nicotine, heparin, and ASA have been or are currently under consideration as deliverable from the surface or from within voids in a stent wall or stent coating.

Much research has been conducted to determine dosage, dose delivery rate, drug action control, drug take up and time duration of delivery and desired targeting of specific cell communities within the arterial wall. Treatment of and retention of drug within endothelium, intima, media, adventia as well as vasa vasorum have been investigated. The physical features of the catheter described in this invention as well as the application of forces from the balloon itself can be altered or adjusted to accommodate parametric requirements such as dosage, delivery rate and depth of treatment within the layers of the blood vessels.

It must be recognized that the spines can pretreat or post-treat a stent deployment site. Or alternatively the device and method can form an independent therapy.

FIG. 4a depicts a shape memory polymer surface 49 which overlays an unperforated balloon surface 19. When thermally activated as seen in FIG. 4b the micro surface expands to the "programmed height" h.

FIG. 5a and FIG. 5b should be considered together. In this alternative embodiment of the invention the proximal end 100 of the device 102 provides for the insertion of a guide wire 104 through a guidewire port 105 and provides for inflation of a distal balloon though an inflation port 106.

The distal end 108 of the device 102 has a balloon 110 which can expand a super elastic metal web 112 that forms a set of small spikes or spines typified by spine 114. The elastic nature of the web 112 allows the web to form a compact low profile shape seen in FIG. 5b when the balloon 110 is deflated. A retractable sheath 116 can be advanced of the web as seen in FIG. 5b to shield the vessel walls from contact with the spines during navigation to the treatment site.

Figure 6A:
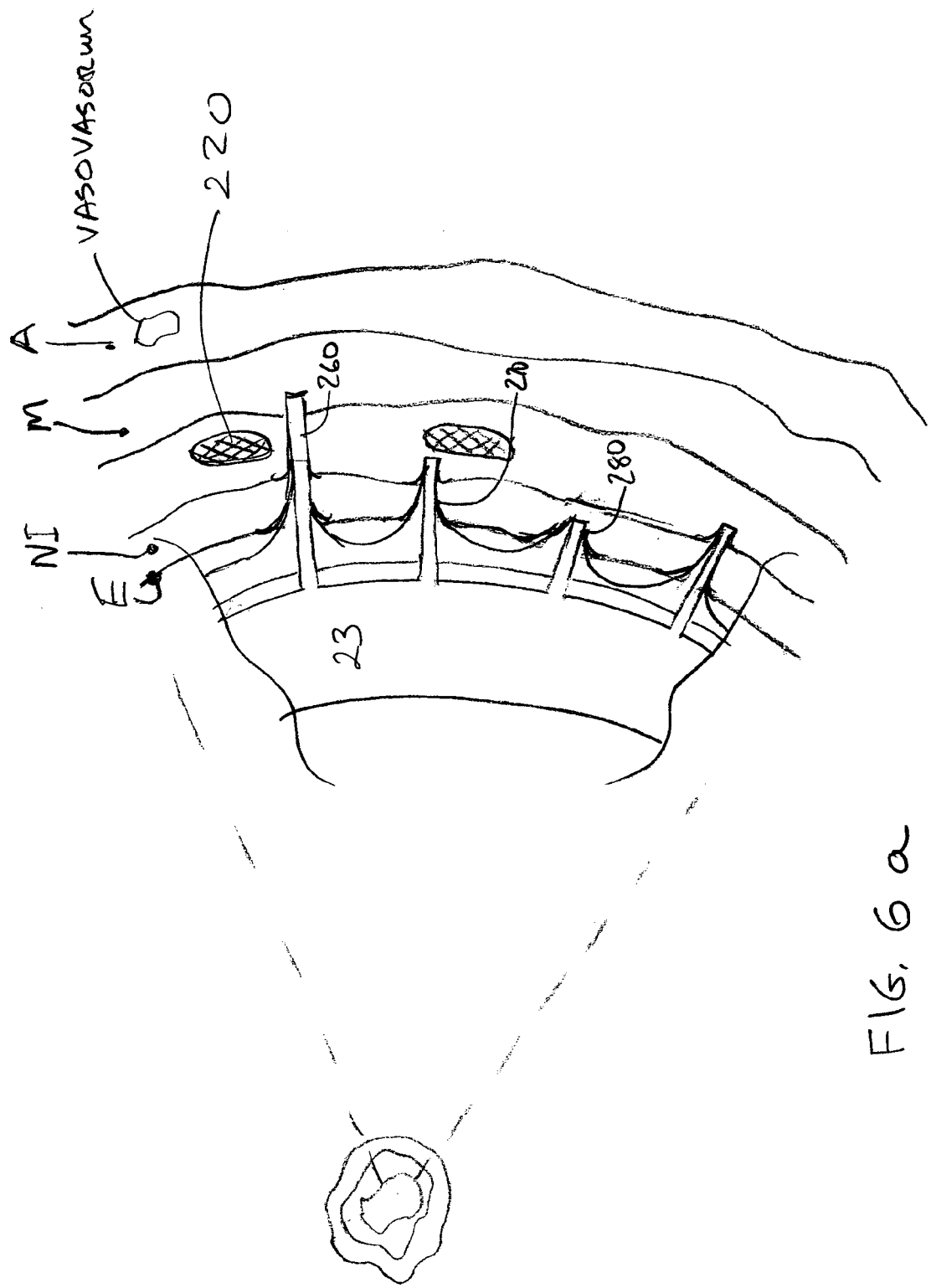
FIG. 6a is a view of a portion of the device in a vessel.

FIG. 6a shows a drug delivery embodiment with a representative spine 280 engaged in the neointima of a vessel. In this figure several spines of differing height are depicted showing drug delivery into each of the several layers of the vessel. It should be understood that the preferred devices all deliver drug therapy or injury to one presented level of tissue. The regions 220 represent sections of a stent. In this application the device is delivering a drug from reservoir 23 to aid in the stent therapy.

Figure 6B:
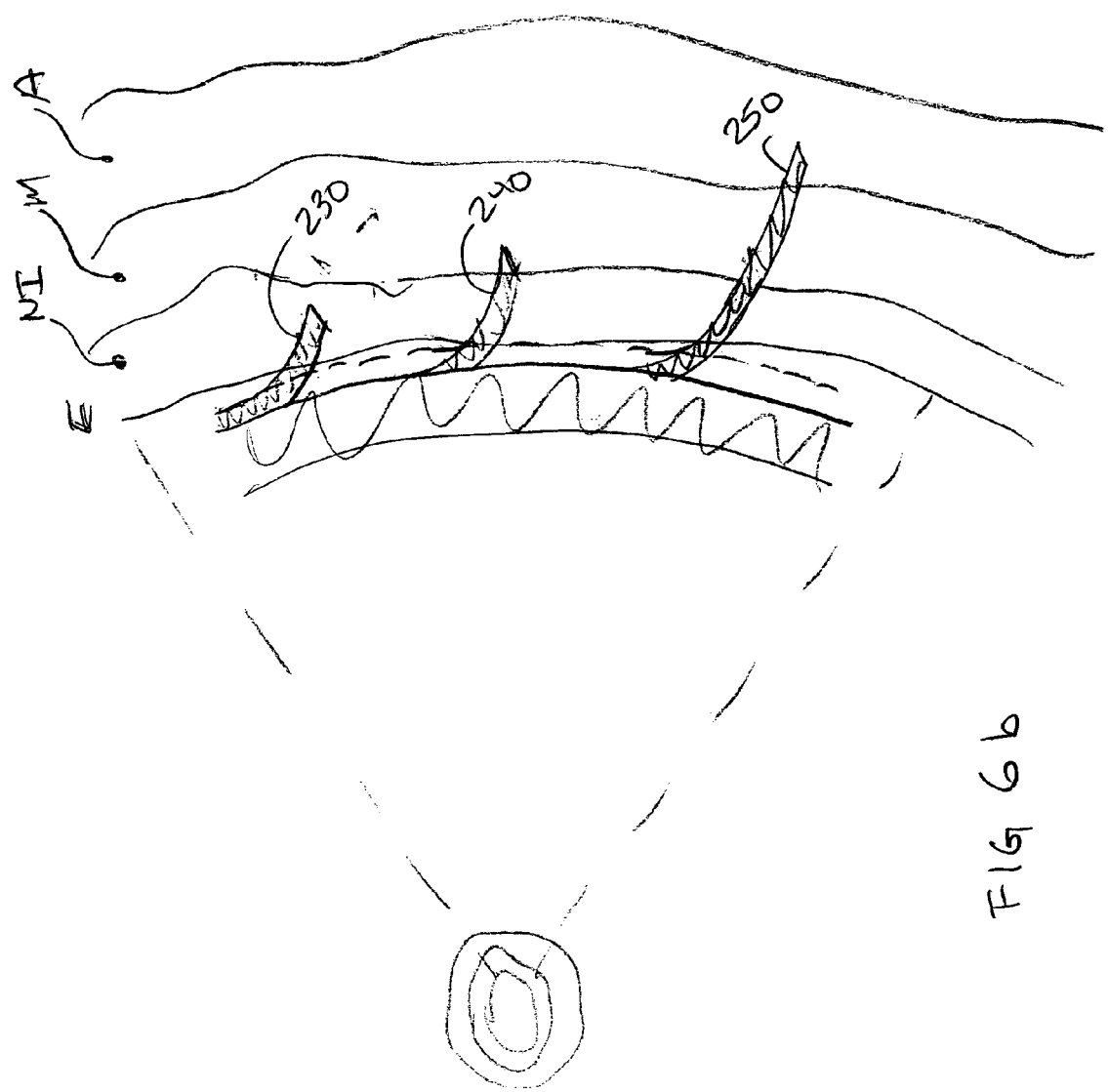
FIG. 6b is a view of a portion of the device in a vessel.

FIG. 6b is an example of the use of the device set forth in FIG. 5a and FIG. 5b to treat the neointima without a drug. In this figure several spines of differing height are depicted including spines 230 240 and 250 showing drug delivery and or injury into each of the several layers of the vessel. It should be understood that the preferred devices all deliver therapy to one presented level of tissue.

Figure 7:
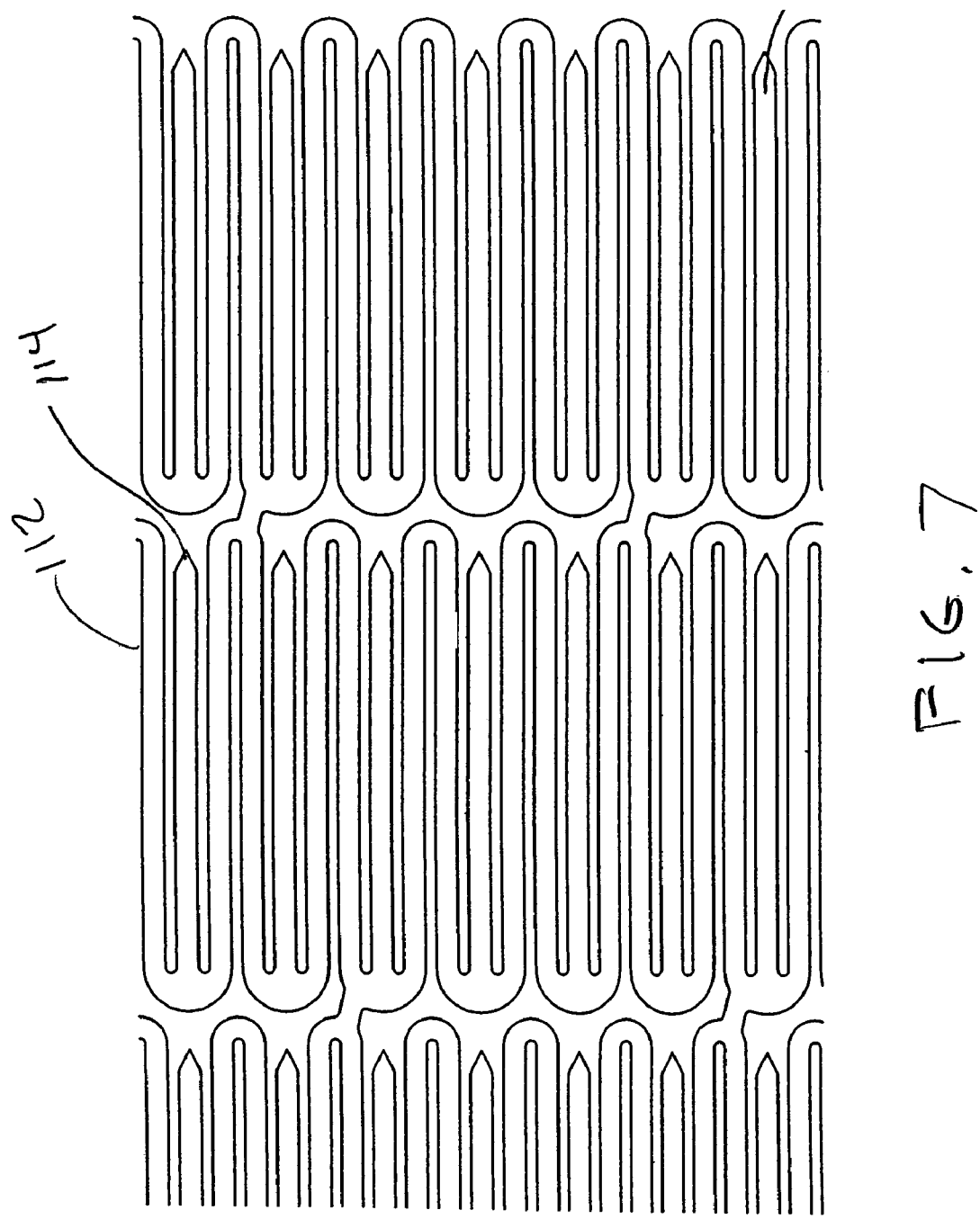
FIG. 7 is a view of a portion of an embodiment of the device.

FIG. 7 is a plan view of the web 112 showing the interconnections of the spines typified by spine 114.

What is claimed is:

1. An intravascular catheter device comprising:
   an elongate catheter body having a proximal end and having a distal end; an exterior deployment balloon having a thermally activated surface having surface features having a nominal height of between about 10 and 120 microns, said surface located proximate said distal end of said catheter body, wherein said thermally active surface includes a plurality of shape memory plastic spines/tines having a first retracted position corresponding to a first temperature, and a second deployed position;
   an interior deployment balloon located inside said exterior deployment balloon;
   said interior balloon and said exterior balloon together forming and defining a drug reservoir between the opposed surfaces of said balloons;
   a plurality of drug release apertures proximate said thermally activated surface communicating with said drug reservoir;
   a fluid supply lumen in said catheter body coupled to said interior deployment balloon for inflating said interior deployment balloon to expand it and to pressurize the drug in said reservoir to assist in delivering the drug.

2. An intravascular catheter device comprising:
   an elongate catheter body having a proximal end and having a distal end;
   an exterior deployment balloon having a thermally activated surface, located proximate said distal end of said catheter body;
   said thermally activated surface includes;
   a plurality of shape memory plastic spines/tines having a first retracted position corresponding to a first temperature, and a second deployed position;
   an interior deployment balloon located inside said exterior deployment balloon;
   said interior balloon and said exterior balloon together forming and defining a drug reservoir between the opposed surfaces of said balloons;
   a plurality of drug release apertures proximate said thermally activated surface communicating with said drug reservoir;
   a fluid supply lumen in said catheter body coupled to said interior deployment balloon for inflating said interior deployment balloon to expand it and to pressurize the drug in said reservoir to assist in delivering the drug;
   said drug release apertures are uncovered by said spines when said spines are in said second deployed position.

* * * * *